(12) United States Patent
Liu et al.

(10) Patent No.: US 7,963,148 B2
(45) Date of Patent: Jun. 21, 2011

(54) GAS SENSOR MADE OF FIELD EFFECT TRANSISTOR BASED ON ZNO NANOWIRES

(75) Inventors: Wei-Long Liu, Yunlin County (TW); Wen-Jauh Chen, Yunlin County (TW); Shu-Huei Hsieh, Yunlin County (TW)

(73) Assignee: National Formosa Univeristy, Douliou, Yunlin County (TW)

( * ) Notice: Subject to any disclaimer, the term of this patent is extended or adjusted under 35 U.S.C. 154(b) by 499 days.

(21) Appl. No.: 12/230,662

(22) Filed: Sep. 3, 2008

(65) Prior Publication Data
US 2010/0050745 A1    Mar. 4, 2010

(51) Int. Cl.
*G01N 7/00* (2006.01)
(52) U.S. Cl. ........................................ 73/31.06
(58) Field of Classification Search .................. None
See application file for complete search history.

(56) References Cited

U.S. PATENT DOCUMENTS

| 5,389,215 | A | * | 2/1995 | Horiuchi et al. | ............... 205/775 |
| 2002/0057610 | A1 | * | 5/2002 | Baliga | ........................... 365/200 |

* cited by examiner

*Primary Examiner* — Hezron Williams
*Assistant Examiner* — Alex Devito
(74) *Attorney, Agent, or Firm* — Bacon & Thomas, PLLC

(57) ABSTRACT

The present invention discloses a gas sensor made of field effect transistor based on ZnO nanowires (ZnO-FET) which operates according to the principle of metal-oxide-semiconductor field effect transistor (MOSFET) and has a charge carrier channel made of ZnO nanowires between source and drain. The gas sensor device disclosed in the present invention has three electrodes-gate, source and drain, so that it is different from the known gas sensor device which has only two electrodes-cathode and anode. The ZnO nanowires as charge channel in the gas sensor device of the present invention is an n-type semiconductor with high specific surface area, and its electric resistance can be controlled by the gate bias, so that the capability of the present device for sensing gas can be largely promoted.

7 Claims, 3 Drawing Sheets

GAS SENSOR MADE OF FIELD EFFECT TRANSISTOR BASED ON ZNO NANOWIRES

FIELD OF THE INVENTION

The present invention relates to a gas sensor device, especially to a gas sensor device based on the principle of field effect transistor. The gas sensor device has three electrodes: source, drain, and gate, and charge channel made of ZnO nanowires between source and drain. Due to the high specific surface area and the gate bias controlling for the electric resistance of ZnO nanowires, the gas sensor device disclosed in the present invention is superior to the known device in sensing gas.

DESCRIPTION OF THE PRIOR ART

There are more and more gases with flammability, explosibility, toxicity created in the human living space along with the science progress and technology development. In order to reduce the environmental contamination and promote the safety of human life, it is necessary to detect and control these harmful gases. Therefore, the studying and manufacturing of the gas sensor device for various gases are needed and urgent [1].

Among the various gas sensor devices, the semiconductor gas sensor is more and more paid attentions and extensively investigated by the world due to its low cost, small volume, simple construction, and high sensibility. There are many oxides such as $SnO_2$, ZnO, $Fe_2O_3$, $WO_3$, Mn, and CrO used as the semiconductor materials for the gas sensors.

In the process of sensing gas for the semiconductor gas sensor, the gas is adsorbed on the surface of semiconductor. If the electron affinity of gas molecular is larger than the work function of semiconductor, the electrons on the semiconductor surface would be transferred to the gas molecular, so the latter would become cathodic ion. Such a gas like $O_2$ and $NO_x$ is called oxidizing gas. Reversely, if the electron affinity of gas molecular is smaller than the work function of semiconductor, the electrons on the gas molecular would be transferred to the semiconductor so the former would become anodic ion. Such a gas like $H_2$, CO, and $C_2H_5OH$ is called reducing gas.

There are four types of mechanisms proposed up to date for explaining the behavior of sensing gas for the semiconductor materials. They are volume control, surface adsorption, grain boundary barrier, and oxygen adsorption mechanisms. The mechanism of oxygen adsorption is proposed from the combination of surface adsorption and grain boundary barrier mechanisms and is one of the most extensively accepted. The oxygen adsorption mechanism can be briefly described as follows.

When the semiconductor materials are in air, the oxygen molecular in air can be adsorbed on the semiconductor surface. The electrons affinity of oxygen molecular is larger than that of semiconductor, so the electrons would be transferred form semiconductor to oxygen molecular, as shown in the following formula.

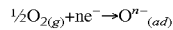

Where $O^{n-}_{(ad)}$ is the adsorbed oxygen and carries negative charges.

When the semiconductor of which surface has adsorbed oxygen is put in the gas to be sensed, the gas to be sensed would react with the adsorbed oxygen. For example, the reaction for $H_2$ is as the following.

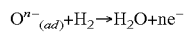

The released electrons $ne^-$ would be transferred to semiconductor, so the electric resistance of semiconductor would vary accordingly. The kind and concentration of sensed gas can be determined from the electric resistance variation of semiconductor.

The necessary condition for a semiconductor as a good sensing material is high sensitivity, strong selectivity, good stability, short time for response and recovery. The n-type semiconductor of ZnO is a potential material for the urage of sensing gas. It can be used for sensing reducing gas, oxidizing gas, and flammable gas such as $C_2H_5OH$, $C_6H_6$, ..., etc.

The sensing function of gas sensor is by means of the adsorption effect between semiconductor surface and gas molecular, so the more the surface area of semiconductor, the more the performance of sensing gas, in other words, the semiconductor material with smaller size is more suitable for gas sensor. For the present, it is a trend to make use of nanosized ZnO as the material for sensing gas.

ZnO is a semiconductor of II-IV compound with a energy gap of 3.4 eV. It has a wurtzite symmetrical center, so it possesses piezoelectricity There are many methods for preparing nanosized ZnO of quasi-one-dimension (QID). The QID nanosized ZnO is generally a single crystal and has an axis along [0001] direction. Due to the oxygen deficiency and the zinc interstitial defect, ZnO is an n-type semiconductor. The charge carrier mobility of QID ZnO is 20~100 $cm^2/V \cdot s$ and can reach 4000 $cm^2/V \cdot s$ after surface treatment [12]. In addition to the energy gap of 3.4 eV, ZnO has exciton binding energy of 60 meV, so it is suitable for the photoelectric application in short wave. Moreover, the electric resistance of QID ZnO is quite sensitive in response to some gases, so it can be also applied to gas sensing.

The ZnO nanotetrapods after $Pd^{2+}$ dopping can be used to sensing ammonia [2]. The nanosized ZnO in wire shape has a better sensing performance for $H_2$ than those in tube and rod shapes [3]. The performance of nanosized ZnO in rod shape for sensing $H_2S$ and $C_2H_5OH$ is determined by the preparing process [4]. The ZnO nanorod formed by hydrothermal process without any treatment has better sensing selectivity and stability than the traditional materials [5]. The quartz crystal microbalance (QCM) formed by ZnO nanowires deposited on the surface of quartz electrode can sensing ammonia [6]. The ZnO nanorod about 95 nm in diameter has been shown that it has quite high sensitivity and selectivity in sensing $C_6H_6$ and $C_2H_5OH$ [7]. When the transparent thin film of ZnO is formed on Si and glass substrates, its performance for gas sensing is much affected by the surface morphology, especially the roughness and grain size [8]. The porous ZnO nanoparticle formed in autoclave is superior to the general ZnO nanoparticle in sensing organic gases [9]. The electric resistance of ZnO film doped with Cu by co-sputtering process has an obvious change in 6 ppm CO at 150° C. This displays the materials has potentiality in gas sensing [10]. The junction between p-type ZnO and n-type ZnO behaves like a tunneling diode, which is sensitive for sensing $H_2$ at 400° C. [11].

In the past decade QID semiconductor has been much noticed and studied by the world due to its high potentiality in the application for nanosized electronic and photoelectric devices [13-17]. When the size of materials is reduced to nanometer scale, the packing density of device can be increased, the consumed power can be decreased, and the sensitivity of surface can be much promoted. Comparing with bulk material, QID material has larger specific surface area and its size also approach the Debye screen length. Its electric property can be largely varied due to the surface states created by the adsorption so that its sensitivity can be largely increased.

Speaking about field effect transistor (FET), there are three types of different structures: junction field effect transistor (JFET), metal-semiconductor field effect transistor (MOSFET), and metal-insulator-semiconductor field effect transistor (MISFET). If the insulator in MISFET is formed by $SiO_2$, the MISFET is then called as metal-oxide-semiconductor field effect transistor (MOSFET), which is one of the most extensively used electronic device for present.

In most MOSFET, the semiconductor is made of Si, the insulator is made of $SiO_2$ and the metal or heavily dopped polysilicon is used as gate. As shown in FIG. 1, the charge carrier (electron or hole) channel (c) is at the interface between $SiO_2$ insulator (d) and Si semiconductor (a). At the two sides of channel (c) are the source (b1) and drain (b2) which are formed by metal or heavily dopped polycrystalline silicon. The flow of charge carrier through the channel can be controlled by the gate (e) bias. In other words, a small variation of gate voltage can much affect the electric current between source and drain. Due to this characteristics MOSFET has two fundamental functions—magnifying and switching.

There are three types of the known gas sensor devices—sintering type, thick film type, and thin film type. The sintering type of gas sensor device is one of the most mature and extensively used. It is made from semiconductor powder added with catalyst and adhesive by using powder metallurgical technology. The thick type of gas sensor device is made by using screen printing technology. The measuring electrode, heating electrode, and sensing paste containing semiconductor, catalyst, and adhesive are first printed on ceramic substrate and then sintered. For the process of making thin film type of gas sensor device, a thin sensing film is first coated on a ceramic substrate by vacuum thin film technology and an electrode is then formed on the film.

For all the conventional gas sensor devices as stated above, there are only two electrode—positive and negative—for measuring. Between the positive and negative electrodes is a semiconductor for sensing of which electric resistance can vary with the type and concentration of gas adsorbed on its surface so that the electric current flowing through the positive and negative electrodes also vary accordingly. Therefore, the type and concentration of sensed gas can be determined basing on the characteristics and the conventional gas sensor device is then called two-electrode-typed gas sensor device.

The device in the present invention is designed basing on the principle of FET and can be called three-electrode-typed gas sensor device. Addition to the positive and negative electrodes, i.e. source and drain, there is a gate, and a charge carrier channel between source and drain is made from ZnO nanowires. Because the gate bias can strong affect the electric current through from source to drain and the ZnO nanowire of channel has a large specific surface area and a character of semiconductor, the performance of the device in the present invention for gas sensing can be largely promoted.

REFERENCE

[1] Jia Grace lu, Paichun Chang and Zhiyong Fan, Materials Science and Engineering: R: Reports Volume 52(2006) 49.
[2] Xiaohua Wang, Jian Zhang, Ziqiang Zhu, Jianzhong Zhu, Physicochem. Eng. Aspect 276(2006) 59.
[3] Chandra Sekhar Rout, A. Hari Krishna, S. R. C. Vivekchand, A. Govindaraj, V. N. R. Rao, Chemical Physics Letters 418(2005) 586.
[4] Caihong Wang, Xiangfeng Chu, Mingmei Wu, Sensors and Actuators B 113(2005) 320.
[5] Xu Jiaqiang, Chen Yuping, Chen Daoyong, Shen Jianian, Sensors and Actuators B 113(2006) 526.
[6] Xiaohua Wang, Jian Zhang, Ziqiang Zhu, Applied Surface Science 252(2006) 2404.
[7] Yuzhen Lv, Lin Guo, Hubin Xu, Xiangfeng Chu, Physica E (2006).
[8] M. Suchea, S. Christoulakis, K. Moschovis, N. Katsarakis and G. Kiriakidis, Thin Solid Films 515(2006) 551.
[9] Hongyan Xu, Xiulin Liu, Deliang Cui, Mei Li, Minhua Jiang, Sensors and Actuators B 114(2006) 301.
[10] H. Gong, J. Q. Hu, J. H, Wang, C. H. Ong, F. R. Zhu, Sensors and Actuators B 115(2006) 247.
[11] S. K. Hazra and S. Basu, Sensors and Actuators B 117(2006) 177.
[12] P. C. Chang, Z. Y FaN, J. G. Lu, appl. Phys. Lett. (2006), submitted for publication.
[13] S. J. Tans, A. R. M. Verschueren, and C. Dekker, Room-temperature transistor based on a single carbon nanotube, Nature, vol. 393, pp. 49-52, 1998.
[14] X. Liu, C. Lee, C. Zhou, and J. Han, Carbon nanotube field-effect inverters, Appl. Phys. Lett., vol. 79, pp. 3329-3331, 2001.
[15] Y Huang, X. Duan, Y Cui, J. Lauhon, K.-H. Kim, and C. M. Lieber, Logic gates and computation from assembled nanowire building blocks, Science, vol. 294, pp. 1313-1317, 2001.
[16] X. Duan, Y Huang, Y. Cui, J. Wang, and C. M. Lieber, Indium phosphide nanowires as building blocks for nanoscale electronic and optoelectronic devices, Nature, vol. 409, pp. 66-69, 2001.
[17] Zhiyong Fan and Jia G Lu, Chemical Sensing With ZnO Nanowire Field-Effect Transition, IEEE Transactions on Nanotechnology, Vol. 5 (2006) pp. 393.

SUMMARY OF THE INVENTION

The present invention discloses a ZnO nanowire FET gas sensor device which has three electrodes and is different from the conventional two-electrode-type device. The device in the present invention is made basing on the principle of FET. In the device there is a gate in addition to the source and drain and a charge channel of ZnO nanowire between source and drain. Because the ZnO nanowire as charge channel is a semiconductor and has a large specific surface area, and the electric resistance between source and drain can be controlled by the gate bias, the performance of the device for the gas sensing can be largely promoted.

For the device of the present invention, a Si wafer is taken as the substrate. On the substrate a layer of $SiO_2$ film is grown in a furnace for the diffusion barrier between Si and Cu. A layer of Cu film as gate is coated on $SiO_2$ film. On the Cu film a layer of $Si_3N_4$ film is deposited as the insulator. On the $Si_3N_4$ film a layer of ZnO nanowire film is coated and a lager of Cu film is deposited on the ZnO nanowire film. A trench is formed in the Cu films and the Cu films at the two sides of trench are used as source and drain, respectively. The ZnO nanowire under the trench and across the source and drain is the charge channel. Moreover, a layer of Ni—Cr alloy film is coated on the back side of Si wafer, which is further etched and formed to a curved Ni—Cr wire for the use of heating.

The ZnO nanowire FET gas sensor device disclosed in the present invention has a small size and is essentially an electronic device like MOSFET. Except for Si substrate, the metal, insulator, and semiconductor are thin films from nanometer to micrometer in thickness. The ZnO nanowire can used the gas sensing material and the charge carrier channel. The ZnO nanowire is an n-type semiconductor itself and has a large specific surface area. Therefore, the gas sensor device made from ZnO nanowire FET disclosed in the present invention has the advantages as follows: (1) small size, light weight, and little material needed; (2) low manufacturing cost due to the utilization of the known semiconductor technology; and (3) high performance for sensing gas.

BRIEF DESCRIPTION OF THE DRAWINGS

For describing in detail the gas sensor device of ZnO nanowire FET disclosed in the present invention, there are some accompanying drawings, wherein:

FIG. 5(*b*) is a energy dispersive spectrum (EDS) of the present invention.

FIG. 5(*c*) is a transmission electron microscope (TEM) bright field image of the present invention.

FIG. 5(*d*) is an electron diffraction pattern of the ZnO nanowire used in the ZnO-FET gas sensor device disclosed in the present invention.

DETAILED DESCRIPTION OF THE PREFERRED EMBODIMENT

Figure 1:
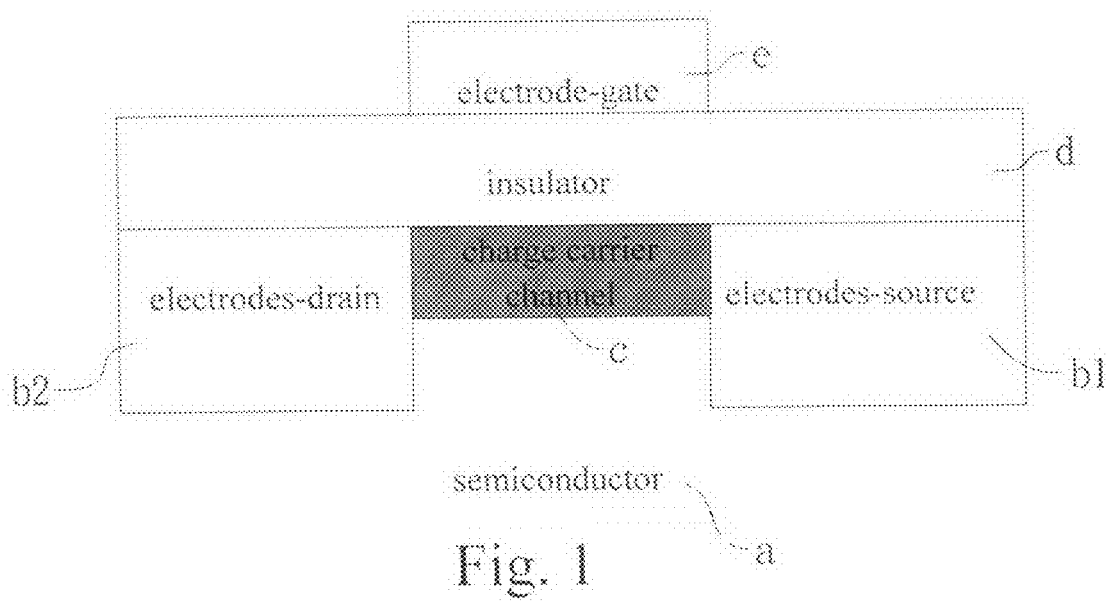
FIG. 1 is a schematic diagram for showing the structure of metal-oxide-semiconductor field effect transistor (MOSFET).
Figure 2:
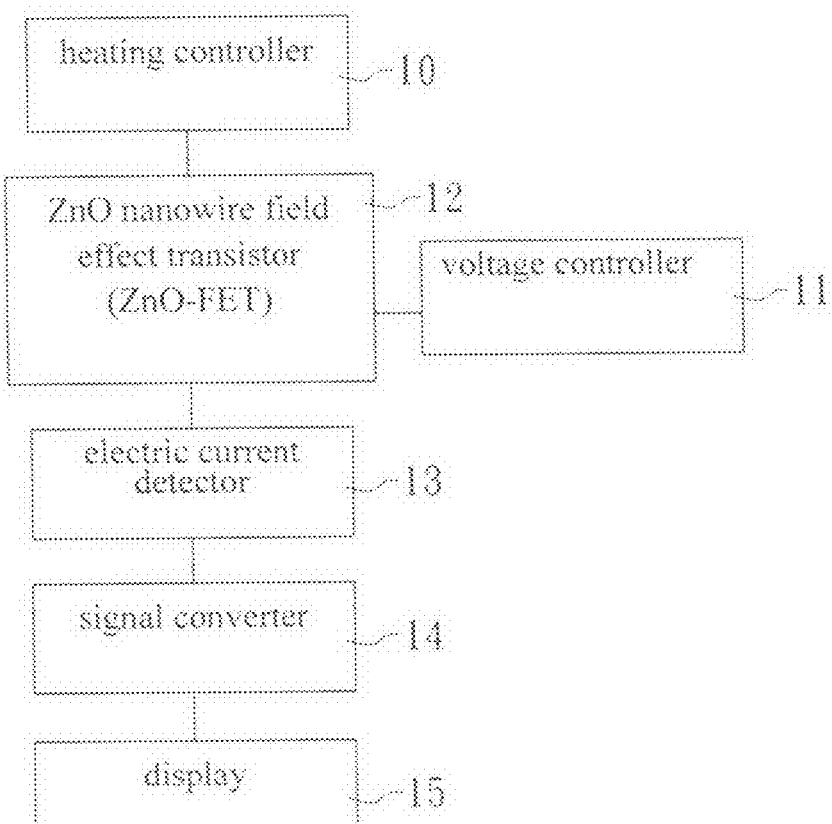
FIG. 2 is a schematic diagram for showing the gas sensor device of ZnO nanowire field effect transistor (ZnO-FET) disclosed in the present invention and the peripheric equipments.

The gas sensor device made of ZnO nanowire field effect transistor (ZnO-FET) disclosed in the present invention and its peripheric equipments are show in FIG. 2. The peripheric equipments needed in the present invention contains heating controller (10), voltage controller (11), electric current detector (13), signal converter (14), and display (15). These peripheric equipments are the known devices so they do not belong to the claims of the present invention. Here only briefly state their function, and the statement about their structure is then omitted.

The heating controller (10) is used for heating the ZnO-FET and keeping the ZnO-FET at constant temperature. The heating controller (10) consists of an power supply, a thermometer, and an auto-thermo controller. The voltage controller (11) is used for controlling the voltages of gate, source, and drain. The electric current detector (13) is used to detect the current flowing between source and drain of ZnO-FET. The signal converter (14) is used for converting the electric current to the gas concentration. The corresponding relation between the electric current and the gas concentration should be pre-stored in the signal converter for the signal conversion.

The display (15) is used to show the result of gas sensing on paper or screen and store the result for using in days to come.

Figure 3:
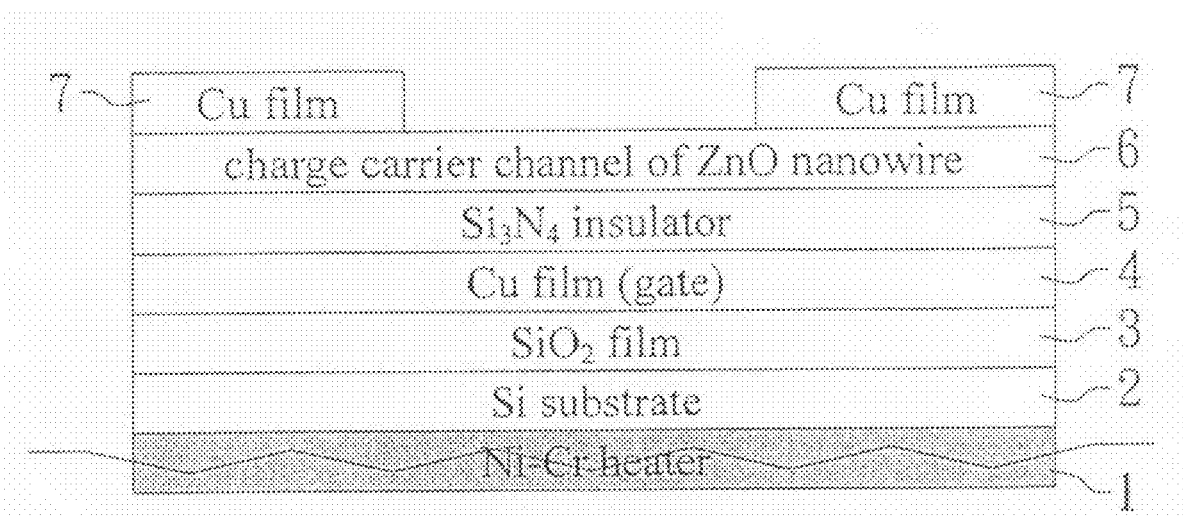
FIG. 3 is a schematic diagram for showing the structure of the gas sensor device made of ZnO nanowire field effect transistor (ZnO-FET) disclosed in the present invention.

FIG. 3 shows the structure of gas sensor device made of ZnO nanowire FET disclosed in the present invention. The substrate (2) is made of Si wafer, and on its surface a $SiO_2$ film (3) is grown in a furnace. A metal film (4) is coated on the $SiO_2$ film, and on the metal film an insulator $Si_3N_4$ film (5) is deposited. On the $Si_3N_4$ insulator is coated a film of ZnO nanowire on which there are two spaced metal films as source and drain (7), and the ZnO nanowires across the source and drain can act as charge carrier channel. Moreover, there is an Ni—Cr wire (1) coated on the back side of Si substrate for the use of heating.

Before the growth of $SiO_2$ film, the Si wafer should have a treatment for cleaning. A base and an acid solution with supersonic vibration are used to remove the grease, organic and nonorganic dirts on the surface of Si substrate. The $SiO_2$ film grown on Si wafer is used as the diffusion barrier between Si and metal of gate. The gate is made of Cu film which is coated on $SiO_2$ film by using electroless plating and vacuum deposition containing thermal evaporation, electron beam evaporation and sputtering deposition. The diffusion between Si and Cu can take place and the copper silicide can be formed at the working temperature, $T \leq 400°$ C., of the ZnO-FET gas sensor device. This would degrade the Cu film as gate. The $SiO_2$ film is about 1 μm in thickness for hindering the inter-diffusion of Si and Cu effectively. The thickness of Cu film is about 0.5 μm which is determined by considering the gate performance and material saving.

The $Si_3N_4$ film on the Cu film gate is used as the insulator of MOSFET. The insulator film can be also made of other insulators such as $SiO_2$, and $Al_2O_3$. The insulator can interrupt the electric connection between gate and source, drain and charge carrier channel. It enable gate to control the resistance of charge carrier channel effectively. The $Si_3N_4$ film can be formed by using sputtering technique.

Figure 4:
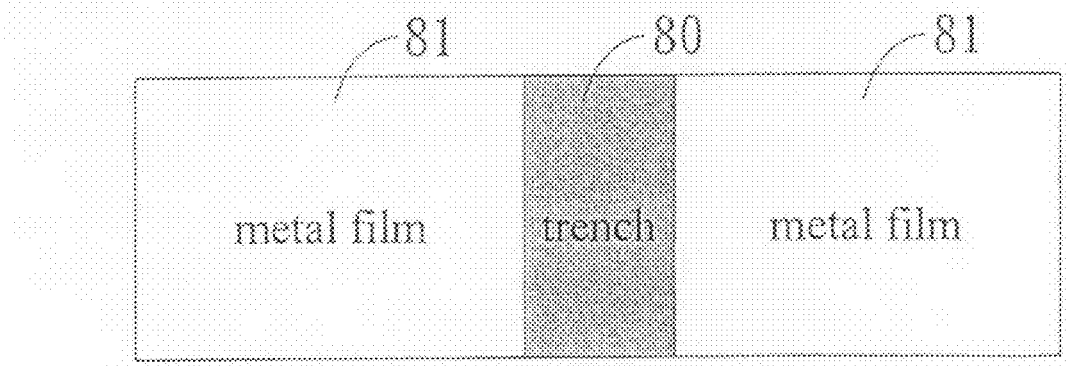
FIG. 4 is a schematic diagram for showing top view of ZnO-FET gas sensor device disclosed in the present invention.
Figure 5A:
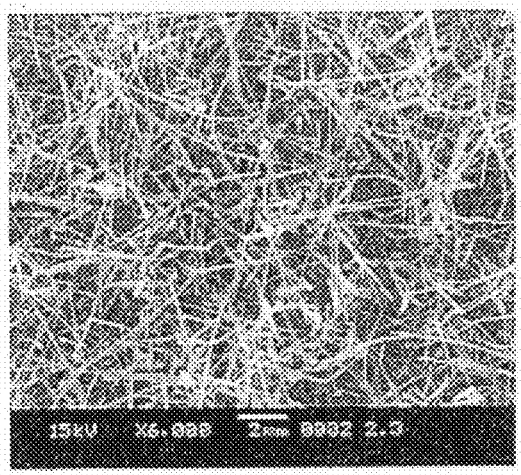
FIG. 5(*a*) is a scanning electron microscope (SEM) image of the present invention.
Figure 5B:
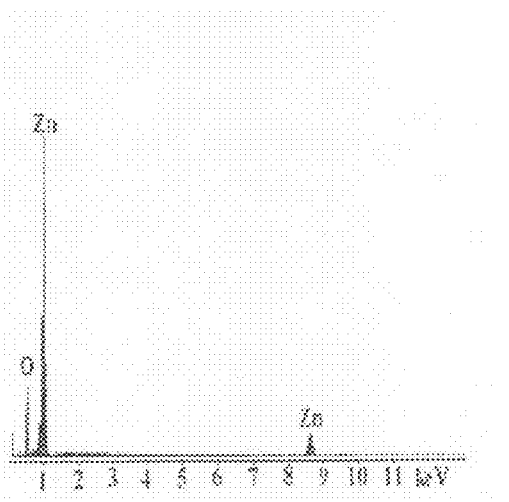
Figure 5C:
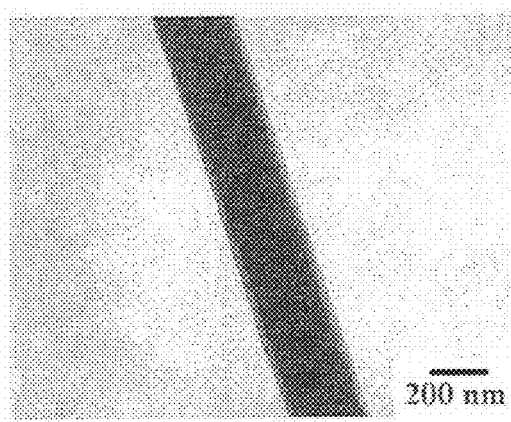
Figure 5D:
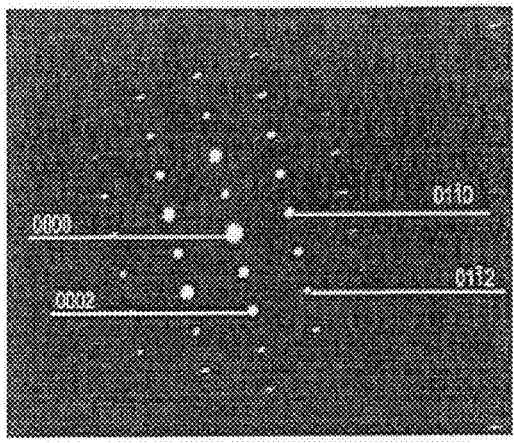

In the process of forming the source, drain and ZnO nanowire film on $Si_3N_4$ insulator, a film of ZnO nanowires is first coated on the $Si_3N_4$ film, a film of Cu metal is then deposited on the ZnO nanowire film, and a trench about 2 μm in width is finally formed on the Cu film by using lithography technology. The ZnO nanowires across the source and drain act as the charge carrier channel. The top view of ZnO-FET gas sensor device is shown in FIG. 4. Under the trench 80 is the ZnO nanowire film 81. The thicknesses of both ZnO nanowire film and Cu film are about 0.5 μm.

FIG. 5 shows the ZnO nanowires used in the ZnO-FET gas sensor device of the present invention. These ZnO nanowires are prepared by chemical vapor deposition (CVD) process in which a brass (Cu—Zn alloy) plate is taken as substrate on which a film of Fe, Co, or Ni is coated as catalyst and the ZnO nanowires are then grown in an atmosphere of $O_2$ or $H_2O$. The scanning electron microscope (SEM) image of the ZnO nanowires is shown in FIG. 5(*a*). The length of ZnO nanowire is over 10 μm. FIG. 5(*b*) is the energy dispersive spectrum (EDS) of the sample of FIG. 5(*a*). The EDS displays the sample consists of pure Zn and O, and the amount of O is smaller than that of Zn so the compound of Zn and O can be deduced as $ZnO_{1-x}$ which is an n-type semiconductor. FIG. 5(*c*) is the transmission electron microscope (TEM) image of one piece of ZnO nanowire. The ZnO nanowire is about 200 nm in diameter. The selected area electron diffraction (SAED) pattern of the sample of FIG. 5(*c*) is shown in FIG. 5(*d*). It displays the ZnO nanowire is a single crystal with hexagonal closed packing (H.C.P) structure.

The trench between source and drain in ZnO-FET gas sensor device of the present invention is only about 2 μm and the ZnO nanowire is over 10 μm in length. Therefore, it is not a problem for the ZnO nanowires to cross the source and drain.

Figure 6:
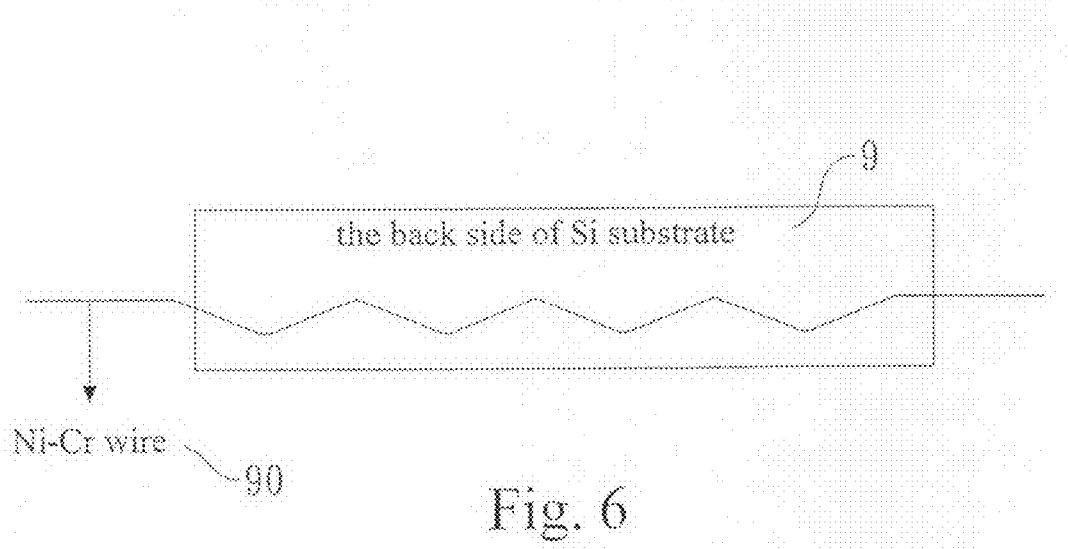
FIG. 6 is a schematic diagram for showing the Ni-Cr wire formed on the back side of Si substrate.

In the process for forming an Ni—Cr wire for heating on the back side of Si substrate 9, a film of Ni—Cr alloy is first coated by sputtering on the back side of Si substrate, and a curved Ni—Cr wire 90 is then formed by lithography technology, as shown in FIG. 6. The Ni—Cr wire 90 is about 1 μm in both thickness and width. An electric voltage can be applied to the two sides of Ni—Cr wire for producing an electric current, therefore, the ZnO-FET can be heated to a preset temperature.

As described above, the ZnO-FET gas sensor device disclosed in the present invention is indeed a novel design and has a high performance in gas sensing, so it can be effectively applied to various fields such as environmental protection, manufacturing industry, and traffic. The present invention possesses novelty, progressivity, and practicability. Although the present invention has been described in detail with reference to accompanying drawings, other modifications in size, material, and partial construction are possible. Therefore, the scope of the appended claims should not be limited to the description contained in the disclosure.

The invention claimed is:

1. A gas sensor device made of ZnO nanowire field effect transistor consisting of:
   (a) a Si substrate;
   (b) a $SiO_2$ film grown on Si substrate;
   (c) an metal film coated on $SiO_2$ film;
   (d) an insulator film deposited on metal film;
   (e) a ZnO nanowire film coated on insulator film;
   (f) two metal electrodes deposited on ZnO nanowire film and spaced by a trench; and
   (g) an alloy wire coated on the back side of Si substrate.

2. A gas sensor device made of ZnO nanowire field effect transistor according to claim 1, wherein the $SiO_2$ film about 1 μm in thickness is directly grown on Si substrate in $O_2$ atmosphere in a furnace, and is used as the diffusion barrier between Si and metal.

3. A gas sensor device made of ZnO nanowire field effect transistor according to claim 1, wherein the metal film about 0.5 μm in thickness may be Cu or Al which is formed on $SiO_2$ film by using electroless plating or vacuum deposition (containing thermal evaporation, electron beam evaporation, and sputtering deposition) and is used as the gate of field effect transistor.

4. A gas sensor device made of ZnO nanowire field effect transistor according to claim 1, wherein the insulator about 20 nm in thickness may be $Si_3N_4$, $SiO_2$, or $Al_2O_3$ which is formed on metal film by using sputtering deposition and is used for interrupting the electric connection between metal film (gate) and source, drain and charge carrier channel.

5. A gas sensor device made of ZnO nanowire field effect transistor according to claim 1, wherein the ZnO nanowire over 10 μm in length is grown on brass (Cu—Zn alloy) substrate in an atmosphere of $O_2$ or $H_2O$ under the catalysis of Fe, Co or Ni, and is across the source and drain and is used as the charge carrier channel of field effect transistor.

6. A gas sensor device made of ZnO nanowire field effect transistor according to claim 1, wherein the two metal electrodes (Cu or Al) about 0.5 μm in thickness as source and drain of field effect transistor is formed by the process in which the metal film is first coated on ZnO nanowire film by vacuum deposition and a trench about 2 μm in width is then formed on the metal film by lithography technology.

7. A gas sensor device made of ZnO nanowire field effect transistor according to claim 1, wherein the alloy wire for heating the ZnO nanowire field effect transistor may be made of Ni—Cr alloy which is formed by the process in which a Ni—Cr alloy film about 1 μm in thickness is first coated on the back side of Si substrate by sputtering deposition and a curved Ni—Cr wire about 1 μm in width is then formed by lithography technology.

* * * * *